United States Patent [19]

Nakao et al.

[11] 3,979,260

[45] Sept. 7, 1976

[54] PRODUCTION OF DEACETOXYCEPHALOSPORIN C

[75] Inventors: Yoshio Nakao; Kazuaki Kitano; Kazuhiko Kintaka; Shigeru Suzuki; Kazuyoshi Katamoto, all of Osaka; Kiyoshi Nara, Kyoto, all of Japan

[73] Assignee: Takeda Chemical Industries, Ltd., Osaka, Japan

[22] Filed: June 14, 1974

[21] Appl. No.: 479,575

[30] Foreign Application Priority Data

| | | |
|---|---|---|
| June 16, 1973 | Japan | 48-68106 |
| Oct. 8, 1973 | Japan | 48-113000 |
| Jan. 16, 1974 | Japan | 49-8098 |

[52] U.S. Cl............................................. 195/36 C
[51] Int. Cl.$^2$.......................................... C12D 9/04
[58] Field of Search ...................... 195/36 R, 36 C

[56] References Cited

UNITED STATES PATENTS

| | | | |
|---|---|---|---|
| 3,239,394 | 3/1966 | Walton | 195/36 R |
| 3,847,742 | 11/1974 | Higgens et al. | 195/36 R |
| 3,862,008 | 1/1975 | Hamill | 195/36 C |

Primary Examiner—Alvin E. Tanenholtz
Attorney, Agent, or Firm—Wenderoth, Lind & Ponack

[57] ABSTRACT

Deacetoxycephalosporin C can be produced with advantage by fermentation of a microorganism which belongs to the genus Streptomyces, Cephalosporium, Emericellopsis, Paecilomyces, Anixiopsis, Arachnomyces or Spriroidium and is capable of producing deacetoxycephalosporin C. Deacetoxycephalosporin C is a useful antibiotic as such or can be used as a starting material for the production of other various cephalosporin antibiotics.

29 Claims, No Drawings

PRODUCTION OF DEACETOXYCEPHALOSPORIN C

This invention relates to a method for producing deacetoxycephalosporin C by fermentation (hereafter in the specification and claims deacetoxycephalosporin C and/or its salt are referred to briefly as DACPC, unless otherwise indicated).

DACPC is a useful antibiotic as such or is used as a starting compound for the production of cephalosporin antibiotics, such as cephalexin, for oral administration, which are clinically highly valued owing to their significant effects upon infections by gram-positive and gram-negative bacteria and also infections by bacteria resistant to various antibiotics. DACPC (free form) is shown by the following formula;

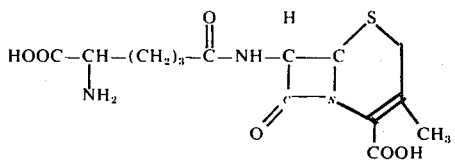

The conversion from DACPC to cephalexin can be achieved by cleaving off the α-aminoadipic acid residue chemically from DACPC to obtain 7-aminodeacetoxycephalosporanic acid and, then, attaching one of various acyl groups to the amino group in position-7 either chemically or enzymatically, for example by the method described in Journal of American Chemical Society 94, 4035 (1972). One of the known methods for producing cephalosporin antibiotics having a 3-methyl group is such that a penicillin obtained by fermentation is chemically caused to undergo ring enlargement to give a cephalosporin compound having a methyl group in position-3 which is then used as a synthetic intermediate for the desired antibiotics. [Journal of American Chemical Society 85, 1896 (1963)].

In another method, cephalosporin C [hereafter sometimes referred to briefly as CPC] from a fermentation process is chemically catalytically reduced to DACPC which is then used as an intermediate for the desired antibiotics. [Journal of medicinal Chemistry 7, 117 (1964)]. However, these methods are invariably combinations of a fermentation process and a chemical process, involving complicated procedures and requiring varied types of equipment, and accordingly are disadvantageous from commercial points of view.

Under these circumstances, extensive research had been conducted by the present inventors to develop a new method by which DACPC might be produced with ease and at low cost. The study led to the finding that microorganisms of the genus Streptomyces, Cephalosporium, Emericellopsis, Paecilomyces, Anixiopsis, Arachnomyces, and Spiroidium accumulate DACPC in the cultured broth.

The present invention is the culmination of the further research made on the basis of this finding.

Thus, the main object of this invention is to provide a new and industrially advantageous method for producing DACPC in a high yield, which comprises cultivating a microorganism, which belongs to the genus Streptomyces, Cephalosporium, Emericellopsis, Paecilomyces; Anixiopsis, Arachnomyces or Spirodium and is capable of producing DACPC, in a culture medium until the DACPC is substantially accumulated in the cultured broth and recovering the DACPC therefrom.

In the practice of the present invention, any of the microorganisms belonging to the genus Streptomyces (e.g. *Streptomyces griseus*, *Streptomyces clavuligerus*, *Streptomyces hygroscopicus*), Cephalosporium (e.g. *Cephalosporium acremonium*, *Cephalosporium polyaleurum* and other species), Emericellopsis (e.g. *Emericellopsis microspora*, *Emericellopsis glabra*), Paecilomyces (e.g. *Paecilomyces carneus*, *Paecilomyces persicinus*), Anixiopsis (e.g. *Anixiopsis peruviana*), Arachnomyces (e.g. *Arachnomyces minimus*) or Spiroidium (e.g. *Spiroidium fuscum*) can be employed insofar as it is able to elaborate DACPC.

Thus, the following microorganisms are examples among others advantageously employable for the process of the present invention.

*Streptomyces griseus* U-25 (IFO-13550, FERM-P No. 2094, ATCC-31031)
*Streptomyces clavuligerus* C-778 (IFO-13548, FERM-P No. 2093)
*Streptomyces hygroscopicus* U-442 (IFO-13598, ATCC-31039) *Cephalosporium sp.* (ATCC-11550)
*Cephalosporium sp.* (ATCC-14553)
*Cephalosporium acremonium* C-3900 IFO-9756, FERM-P No. 2287)
*Cephalosporium acremonium* K-186 (IFO-9918, ATCC-20416)
*Cephalosporium polyaleurum* Y-505 (IFO-9535, FERM-P No.1160, ATCC-20360)
*Cephalosporium polyaleurum* 7-64 (IFO-9920, ATCC-20415)
*Cephalosporium polyaleurum* 199 (IFO-9394, FERM-P No. 1159, ATCC-20359)
*Emericellopsis microspora* 15121 (IFO-9728, FERM-P No. 2095)
*Emericellopsis microspora* K-163 (IFO-9922, ATCC-20422)
*Emericellopsis glabra* (IFO-9031)
*Emericellopsis glabra* IFO-9033
*Emericellopsis glabra* IFO-9034
*Paecilomyces carneus* C-2237 (IFO-9729, FERM-P No. 2096, ATCC-20417)
*Paecilomyces carneus* C-4053 (IFO-9730, FERM-P No. 2098)
*Paecilomyces persicinus* C-3009 (IFO-0731, FERM-P No. 2097, ATCC-20418)
*Anixiopsis peruviana* C.B.S.-301.67
*Anixiopsis peruviana* K-21 (IFO-9916, ATCC-20419)
*Arachnomyces minimus* C.B.S.-324.70
*Arachnomyces minimus* K-154 (IFO-9917, ATCC-20420)
*Spiroidium fuscum* IFO-5479
*Spiroidium fuscum* K-461 (IFO-9923, ATCC-20421)

The numbers in the parentheses attached to the abovementioned strains and indicated by IFO, FERM-P, CBS or ATCC are the accession numbers at Institute for Fermentation, Osaka, Japan (IFO); the Fermentation Research Institute of the Agency of Industrial Science and Technology, Chiba, Japan (FERM); Centraalbureau voor Schimmelcultures, Holland (CBS); and American Type Culture Collection, U.S.A. (ATCC), respectively.

The microbiological characteristics of these strains are as follows.

A. *Streptomyces griseus* U-25

1. Morphological characteristics
   a. Mode of branching of sporogenous hyphae:
      Monopodially branched; tufts formed.
   b. Configuration of sporogenous hyphae:
      Rectus-flexibilis.
   c. Number of spores:
      Not less than 10.
   d. The surface structure and size of spores.
      Smooth, 0.8 by 0.8–1.2 $\mu$.
   e. Flagellum:
      Not observed.
   f. Sporangium:
      Not observed.
2. Growth characteristics on various media
   The results of cultivation at 28°C over a period of 1 to 3 weeks are shown in Table 1.

4. Assimilation of carbon sources (at 28°C on Pridham-Gottlieb agar)
   +: L-arabinose, D-glucose, D-fructose, D-mannite, D-xylose
   ± or −: Sucrose, inositol, L-rhamnose, raffinose A comparison of the characteristics listed above with the descriptions of Bergey's "Manual of Determinative Bacteriology", (7th ed.), S. A. Waksman's "The Actinomycetes", (vol. 2) and "International Journal of Systematic Bacteriology" shows that strain U-25 belongs to the genus Streptomyces of the family Streptomycetaceae. The U-25 strain has characteristics in fair agreement with the descriptions of *Streptomyces griseus*, though it is slightly different in the utilization of carbon sources. Therefore, this strain has been identified as a strain belonging to *Streptomyces griseus*.

B. *Streptomyces hygroscopicus* U-442

1. Morphological characteristics
   Aerial mycelium is generally short, monopodially Table 1

| Type of medium | Growth | Vegetative mycelium | Aerial mycerium | Reverse | Soluble pigment |
|---|---|---|---|---|---|
| Sucrose nitrate agar | poor to moderate | Colorless | Fair, powdery; white to cream | Light yellowish orange | None |
| Glucose asparagine agar | Good | Colorless | Abundant, powdery; white to light yellowish tan | Light yellow-tan | Light tan |
| Glycerin asparagine agar | Good | Colorless to cream | Abundant, powdery; ivory with light greenish gray tinge | Light olive | Light olive |
| Starch inorganic salt agar | Moderate | Colorless | Sparse, powdery; dusty yellow | Colorless | Very light olive |
| Tyrosine agar | Good | Colorless | Abundant, powdery; light citron; later becoming reddish (Bisque) | Colorless light ivory | Very light olive |
| Nutrient agar | Moderate | Colorless to cream | Moderate to abundant, powdery; white to light gray | Brownish yellow | None |
| Yeast malt agar | Good | Colorless to cream | Abundant, powdery; citron to Banboo-yellow | Mustard | Cinnamon |
| Oatmeal agar | Good, wrinkled | Colorless to cream | Sparse, powdery; white | Colorless | Mustard |
| Peptone iron yeast extract agar | Moderate, thin growth, glistening | Colorless to cream | Not produced | Colorless | None |

3. Physiological characteristics
Growth temperature: Good growth at 28°–37°C.
Reduction of nitrates: Positive
Liquefaction of gelatin: Positive
Melanin production: Negative branched, having tight spirals in dense clusters. The number of spores in the chain is not less than 10. The shape of spores is ellipsoidal to short-cylindrical, measuring 0.5–0.7 by 0.6–1.1 $\mu$ and their surface of them is smooth. Neither flagellum nor a sporagium is observed.
2. Growth characteristics on various media See Table 2.

Table 2

| Medium | Growth | Aerial mycelium | Reverse | Soluble pigment |
|---|---|---|---|---|
| Sucrose nitrate agar | Good, wrinkled, colorless to pale yellow | Moderate, powdery, white to Olive Gray | Mustard Tan to Mustard Brown | Mustard |
| Glucose asparagine agar | Moderate, colorless to pale yellow | Poor, white or Covert Gray to Dark covert gray | Colorless | None |
| Glycerol asparagine agar | Moderate, restricted, colorless | Moderate, powdery, Natural or, Covert Gray to Beige Gray | Colorless or Slate Tan. | None |
| Starch inorganic salts agar | Moderate, colorless | Abundant, powdery white to Natural, partly hygroscopic | Colorless or cream | None |
| Tyrosine agar | Moderate, colorless | None | Colorless | None |
| Nutrient agar | Moderate, colorless | None | Colorless | None |

Table 2-continued

| Medium | Growth | Aerial mycelium | Reverse | Soluble pigment |
| --- | --- | --- | --- | --- |
| Yeast malt agar | Good, colorless | Abundant, powdery white to Natural, or Covert Gray to Beige Gray, partly hygroscopic | Amber to Topaz | None or Light Amber |
| Oatmeal agar | Good, thick, colorless | Abundant, powdery white to Natural or Beige Gray, partly hygroscopic | Colorless to Light Wheat | None or Bamboo |
| Peptone yeast extract iron agar | Moderate, restricted, colorless | None | Colorless | None |

3. Physiological characteristics

| | | |
| --- | --- | --- |
| (a) | Growth temperature | Good growth at 20–37°C. Optimal temperature is 28–32°C. |
| (b) | Growth pH | Growth occurs within the range of pH 5–9. Optimal pH is 6–7. |
| (c) | Gelatin liquefaction | Not liquefied. |
| (d) | Starch lysis | positive (moderate) |
| (e) | Action on skimmed milk | Not coagulated but weakly peptonized. |
| (f) | Reduction of nitrates | Negative |
| (g) | Melanin - like pigment | Negative |
| (h) | Assimilation of carbon sources (at 28°C on Pridham-Gottlieb agar) | |

+ L.-arabinose, D-glucose, D-fructose, D-mannite, D-xylose, sucrose, inositol, L-rhamnose, raffinose The taxonomical properties of U-442 are summerized as follows;
1. Spore-Chain morphology; Spirales
2. Spore surface; smooth
3. The color of growth; Colorless to pale yellow
4. Aerial mass color; gray color series
5. hygroscopic areas are found in the aerial mycelium.
6. melanin-like pigment; not formed.

From these properties, U-442 was identified as a strain belonging to *Streptomyces hygroscopicus*, compared with the description of Bergey's "Manual of Determinative Bacteriology", 7th ed.; S. A. Waksman's "The Actinomycetes", vol. 2; and "International Journal of Systematic Bacteriology", 22, 265 (1972).

C. Cephalosporium sp. ATCC-14553 and Cephalosporium acremonium K-186

Colonies on malt extract agar and potato dextrose agar, irregular, wrinkled, raised and usually wettish, colorless to pale yellow. Aerial mycelium scanty. Reverse colorless to pale yellow. Soluble pigment yellow. Hyphae 1–3.5 μ, septate. Conidiophores arising as side branches on hyphae, 30–60 μ long, 2.5–3.5 μ width at base. Conidia multi-shaped, elliptical or oblong, straight or curved, hyaline, 6–9 × 2–3 μ. These two strains have different productivities of DACPC, deacetylcephalosporin C[hereafter sometimes referred to briefly as DCPC]and CPC.

D. Cephalosporium polyaleurum 7-64

1. Characteristics on agar media
1. Malt extract agar:
   Growth good, spreading. Aerial mycelium scanty, villous all over, pale yellowish brown. Reverse colorless.
2. Potato agar:
   Growth good, spreading. Aerial mycelium abundant, often bundled into ropes, white to pale brown, with radial folds, villous. Reverse colorless or pale yellow.
3. Czapek's agar:
3. Czapek agar:
   Growth good, spreading. Aerial mycelium abundant, often bundled into ropes, genuine white, villous. Reverse colorless.
4. Oatmeal agar:
   Growth good, spreading. Aerial mycelium scanty, low and flat, villous, light-colored. Reverse colorless to pale yellow.
5. 1% glucose bouillon agar:
   Growth good, non-spreading, with many radial wrinkles. Aerial mycelium abundant, genuine white, villous. Reverse pale yellow.

2. Microscopic morphological characteristics

Extremely scanty formation of conidia. The slender aerial hyphae, 1.0 to 1.5 μ wide, are copiously branched and colorless. Conidiophores extend straight from aerial mycelium, measuring 40 to 60 μ long and 1.0 to 1.5 μ wide but 2 μ wide at the point of attachment. Conidia are ellipsoidal with somewhat pointed ends or asymmetric; one-celled and colorless. Size 1.5 to 2 by 3 to 6μ; clustered in a mass at the extremity of the conidiophore. Many small asexual spores corresponding to aleuriospores are formed directly from the tips and sides of hyphae. Short and sometimes curved, 3 to 4 by 4 to 6μ, colorless. Though two of them are joined at times, they occur singly in many cases.

The formation of conidia is limited to the initial phase of growth and very scanty. On the other hand, many aleuriospores are formed in the intermediate phase and thereafter and are observed all over the colony. No organs for sexual reproduction are observed on any of the media.

The suitable growth temperature is 25°–30°C; the pH is 5.0 to 7.0.

A comparison of the foregoing characteristics of strains k-186, and 7-64 with the descriptions in "Dictionary of Fungi", 6th ed. And Barnett Hunter, "Illustrated Genera of Imperfect Fungi", 3rd ed. indicates clearly that these strains belong to the genus Cephalosporium, the family Moniliaceae, the order Moniliales of Fungi Imperfecti.

In the light of the descriptions in Gilman, "A Manual of Soil Fungi (1957)" and in Sukapure et al., "Mycologia 58, 351 (1966)", strain K-186 has been identified as a strain belonging to *Cephalosporium acremonium*.

Incidentally, strain 7-64 is a strain belonging to a new species which has been designated as *Cephalosporium polyaleurum*.

E. *Emericellopsis microspora* K-163

1. Characteristics on agar media
   1. Malt extract agar:
      Growth good, with radiant wrinkles on the surface, slightly diffusing, colorless to pale salmon pink. Reverse light orange to salmon pink. Aerial mycelium scanty, cottony and white.
   2. Potato glucose agar:
      Growth good, slightly spreading, white to light salmon pink. Reverse yellow to orange yellow. Aerial mycelium abundant, flocculent. Many blackish brown asci are formed.
   3. Czapek's agar:
      Growth good, low and flat. Aerial mycelium villous and white. Reverse light orange.
   4. Sabouraud's agar:
      Growth good, low and flat, slightly spreading, salmon pink. Aerial mycelium flocculent and white. Reverse light orange.
   5. Oatmeal agar:
      Growth good, slightly spreading, salmon pink. Aerial mycelium scanty, flocculent and white. Reverse light orange to salmon pink. Blackish brown asci are formed.
2. Microscopic morphology The microscopic morphology of the strain as grown on the above media follows:

The aerial mycelium, 1.5–2 $\mu$ wide, is branched and colorless. The conidiophore extends straight from the vegetative or aerial mycelium, measuring 30–60 $\mu$ long by 1.5–2.5 $\mu$, with conidia borne at its extremity. The conidium varies in size, 3–8 × 1.5–4 $\mu$, and is oval to oblong.

The ascocarp is dark-colored and substantially spherical, varying in size from about 30 to 60 $\mu$. Each ascus contains 8 ascospores, measuring 9 to 12 $\mu$. The ascospore is oblong to oval and light greenish brown, measuring 3–3.5 by 4–5.5 $\mu$. the spores have wings and appear variously shaped. The length of the wing is 1.5 to 3 $\mu$.

F. *Paecilomyces carneus* C-2237 and C-4053

1. Characteristics on agar media
   1. Malt extract agar:
      Good growth, not so spreading, cushion-like, white to milk brown, occasionally with a pale pink tinge. Reverse yellowish green-brown-deep greenish black, but does not diffuse a green pigment.
   2. Potato agar:
      Good growth, non-spreading. Aerial mycelium flocculent to cushion-like, white. Reverse yellowish green to deep green.
   3. Czapek's agar:
      Good growth, non-spreading. Aerial mycelium flocculent to cushion-like, white to milk white. Reverse yellowish green.
   4. Sabouraud's agar:
      Good growth, non-spreading. Aerial mycelium flocculent to cushion-like and white. Reverse yellowish green to deep green.
   5. Oatmeal agar:
      Good growth, slightly spreading. Aerial mycelium flocculent to cushion-like, occasionally powdery. White to milk white. Reverse yellowish green to deep green.
2. Microscopic morphological characteristics Aerial mycelium, 1.5 to 2 $\mu$ wide, is branched. The conidiophore is formed on aerial mycelium, being single or mono- or biverticillate. About 2 $\mu$ in width. The phialide is elongated-lageniform (shaped like an elongated flask), with its tip extending delicately, forming conidia. Size 15 to 20 by 2 to 2.5 $\mu$. The conidia are elliptical and appear to be finely roughened, measuring 3 to 4 by 2 to 2.5 $\mu$, in long chains. No organs for sexual reproduction are observed on any of the above media. Optimal growth conditions are: 24°–28°C. pH 5–7

G. *Paecilomyces persicinus* C-3009

1. Characteristics on agar media
   1. Malt extract agar:
      Good growth, slightly spreading. Aerial mycelium is flocculent-cottony and occasionally funiculose. White to milk brown and, at times, with pale reddish tinge. Reverse yellow-yellowish brown and does not become green. A yellowish brown pigment is produced in medium.
   2. Potato agar:
      Good growth, non-spreading. Aerial mycelium is cottony to powdery, being white. Reverse light brown.
   3. Czapek's agar:
      Very poor growth. Aerial mycelium is only rudimentary.
   4. Sabouraud's agar:
      Good growth, non-spreading. Aerial mycelium is comparatively sparse, being cottony to powdery and white to light brown. Reverse colorless to light brown.
   5. Oatmeal agar:
      Good growth, slightly spreading into medium. Abundant aerial mycelium villous to cottony and, in many cases, bundled to assume the appearance of ropes. White to light brown, occasionally with light reddish tinge. Reverse yellowish brown to yellowish rose.
2. Microscopic morphological characteristics Aerial mycelium sometimes occurs singly, but at other times several of them are bundled to assume the shape of a rope.

No conidiophore is formed, but phialides are directly formed from the aerial mycelium or ropes of aerial mycelia.

Each phialide is shaped like an elongated flask, measuring 10 to 30 $\mu$ long and, at the point of attachment, 1.8 to 2.2 $\mu$ wide. The phialide bears conidia on its end. The conidium is ellipsodial to ovoid, its surface being smooth or slightly wrinkled. Size 2–3 by 2.5–4.0 $\mu$. Long chains are formed. No organs for sexual reproduction are observed on any of the above media.

The optimal growth conditions are 24° to 28°C and pH about 5 to 7.

According to Ainsworth et al., "Dictionary of Fungi", 6th ed. and Barnet Hunter, "Illustrated Genera of Imperfect Fungi", 3rd ed., the strains C-2237, C-3009 and C-4053, having the foregoing microbiological characteristics fall within the ambit of the genus *Paecilomyces*, the family *Moniliaceae*, the order *Moniliales* of Fungi Imperfecti.

Furthermore, according to "Transactions British Mycological Society" 40, 17–89 (1957), the strains C-2237 and C-4053 seem to belong to *Paecilomyces carneus* Duché et Heim. The strain C-3009, in view of above literature and "Micological Papers" No. 107, 1–23 (1967) of Commonwealth Micological Institute, has been identified to be a strain belonging to *Paecilomyces persicinus* Nicot.

H. *Anixiopsis peruviana* CBS-301.67 and K-21

Strain CBS-301.67 is a known one which is disclosed in CBS-List of Cultures, 28th edition, 1972.

Strain K-21 has similar microbiological characteristics except the productivity of DACPC, deacetylcephalosporin C, and CPC.

These strains are belonging to *Eurotiales-Eurotiaceae-Anixiopsis* and have following properties.

Colonies on malt extract agar or Leonian-yeast extract agar, spreading slowly or not, white to pale brown, later become brown to dark brown by forming perithecia. Reverse, at first yellow to yellowish brown, but later dark brown to nearly black. Soluble pigment, yellow, later olivaceous brown. Hyphae, hyaline, thin-walled, remotely septate branched, 1–2.5 $\mu$ in diameter.

Perithecia cleistocarpous, dark-brown, almost black when dry, in some areas produced beneath aerial mycelium, in others, forming a dense, superficial layer on surface of agar with little aerial mycelium, globose, glabrous except for scanty attachments to aerial hyphae, 140–350 $\mu$ diameter.

Asci in large, closely aggregated clusters, without definite orientation, subglobose, 6.5–8.0 × 5.5–6.5 $\mu$, eight-spored, thin walled, evanescent.

Paraphyses scanty, filamentous, clustered, septate, 2–4 $\mu$ diameter, mixed with asci.

Ascospores discoid, 2.5–3.0 × 2.5–3.0 × 2.0–2.5 $\mu$ in globose mass, minutely echinulate, very pale yellow.

Chlamidospores globose to subglobose, hyaline, smooth, 8–10 $\mu$ with wall slightly thickened, mostly terminal, scattered on hyphae, immersed in hyphal mat, not abundant.

No other conidia or spermatia.

I. *Arachnomyces minimus* CBS-324.70 and K-154

Strain CBS-324.70 is a known one which is disclosed in CBS-List of Cultures, 28th edition, 1972.

Strain K-154 has similar microbiological characteristics except the productivity of DACPC, DCPC and CPC.

These strains belong to *Eurotiales-Eurotiaceae-Arachnomyces* and have following properties.

Colonies on Weitzman and Silva-Hutner's medium attaining a diameter of 2.5 cm in 2 months at room temperature, felty, greenish-yellow, azonate, producing a violet-brown pigment which diffuses into the medium; reverse brown, speckled. Mycelium hyaline, thin-walled, remotely septate, with numerous ampulliform swellings, producing globose cells 7–11 $\mu$ in diameter in the vicinity of the ascocarp initials and ascocarps and occasionally elsewhere.

Ascocarps subglobose to globose, reddish-brown by reflected light, nearly opaque when mature, hairy due to abundant mycelial attachments which disappear at maturity, non-ostiolate, bearing several long hair-like appendages, 100–315 $\mu$ in diameter, breaking open irregularly at maturity.

Ascocarp appendages 2.5–5.5 $\mu$ broad, up to 3 mm or more long.

Asci subgloboase to globose, non-stipitate, evanescent, eight-spored, 5.5–8.5 $\mu$ in diameter. Ascospores oblate, light yellowish-brown by transmitted light, light reddish-brown to claycolored in mass, smooth, 2.8–3.5 × 1.5–2.0 $\mu$. Conidial stage; one.

J. *Spiroidium fuscum* IFO-5479 and K-461

Strain IFO-5479 is a known one which is disclosed in IFO-List of Cultures, fifth edition, 1972.

Strain K-461 has similar microbiological characteristics except the productivity of DACPC, DCPC and CPC.

These strains belong to *Fungi Imperfecti-Moniliales-Moniliaceae-Spiroidium* and have the following morphological properties.

Growth poor or moderate on corn-meal agar or Czapek's agar, and good on malt-agar or glucose bouillon agar.

Colonies at first white, gradually tinged greenish yellow, finally becoming brown, hyphae very fine, 1.5–2 $\mu$ in width, slightly septate, occasionally bundled. Spore-forming hyphae branched with irregular spirals, divided by formation of septa, and gradually formed ohlamidospores. Chlamido spores; square, oblong, or cylindrical, 2–3 $\mu$, often contains oildrop, when germination, often swelled and formed germ tube. Organs for sexual reproductions are not formed on any media.

In cultivating the microorganisms to be employed according to this invention, use is made of a culture medium containing the sources of carbon and the sources of nitrogen which the microorganisms can assimilate.

As carbon sources, for example, glucose, sucrose, maltose, starch, soluble starch, waste molasses, glycerin, various organic acids such as acetic acid, fumaric acid, benzoic acid, etc., various alcohols such as ethanol, butanol, etc., n-paraffins and various oils and fats are employed. As the sources of nitrogen, use can be made of various organic and inorganic ones such as peptone, soybean flour, meat extract, cotton seed flour, dried yeast, yeast extract, corn steep liquor, urea, ammonium salt [e.g. $NH_4Cl$, $(NH_4)_2SO_4$, $NH_4NO_3$, ammonium phosphate], nitrates, (e.g. $NaNO_3$, $KNO_3$), etc.

In addition metallic salts such as sulfates, nitrates, chlorides, carbonates, phosphates and other salts of metals, e.g. K, Mg, Ca, Na, etc., can be incorporated. If necessary, it is further possible to add to the culture medium various substances which are able to encourage the growth and DACPC-producing ability of the microorganism used, such as methionine, cysteine, cystine, thiosulfates, methyl oleate, lard oil, various vitamins, amino acids, nucleic acid-containing materials, etc., in which event the accumulation of DACPC is further increased.

For instance, methionine is very efficient for the production of DACPC by the microorganisms of the genus *Cephalosporium* and *Emericellopsis*, whereas cysteine and/or cystine are (is) very effective for the production of DACPC by the microorganisms of the genus *Paecilomyces*, *Arachnomyces*, *Anixiopsis* and *Spiroidium*. The above effects are proved by the following comparative experiments.

Table 3

| Effect of methionine | | DACPC accumulated (μg/ml) | | | | | |
|---|---|---|---|---|---|---|---|
| | | DL.-Methionine | | | | | |
| Strain | Concentration (%) 0 | 0.01 | 0.1 | 0.3 | 0.5 | 1.0 | 2.0 |
| Cephalosporium sp ATCC 14553 | 20 | 25 | 35 | 70 | 105 | 100 | 30 |
| Cephalosporium acremonium K-186 | 50 | 70 | 500 | 1500 | 1790 | 1900 | 500 |
| Cephalosporium polyaleurum 7-64 | 70 | 90 | 250 | 400 | 560 | 550 | 150 |
| Emericellopsis microspora K-163 | 200 | 240 | 300 | 450 | 540 | 550 | 260 |

Table 4

| Effect of L-cysteine and/or L-cystine | | | | | | | DACPC accumulated (μg/ml) | | | | | |
|---|---|---|---|---|---|---|---|---|---|---|---|---|
| | Compound | L-cysteine | | | | | | L-cystine | | | | |
| Strain | Concentration (%) 0 | 0.01 | 0.1 | 0.3 | 0.5 | 1.0 | 0 | 0.01 | 0.1 | 0.3 | 0.5 | 1.0 |
| Paecilomyces carneus C-2237 | 160 | 190 | 450 | 520 | 500 | 250 | 160 | 180 | 300 | 400 | 420 | 225 |
| Paecilomyces persicinus C-3009 | 90 | 120 | 280 | 310 | 320 | 150 | 90 | 105 | 150 | 220 | 200 | 120 |
| Anixiopsis peruviana CBS-301.67 | 130 | 150 | 200 | 250 | 210 | 175 | 130 | 145 | 180 | 200 | 220 | 160 |
| Arachnomyces minimus CBS-324.70 | 20 | 30 | 80 | 102 | 120 | 45 | 20 | 30 | 80 | 105 | 110 | 45 |
| Spiroidium fuscum IFO-5479 | 50 | 65 | 90 | 145 | 130 | 70 | 50 | 60 | 85 | 115 | 100 | 65 |

In the above experiments each strain was incubated under the condition (e.g. medium, temperature, incubation time, etc.) as shown in the following examples of the respective strains.

As seen from the above experiments an addition of at least 0.01%, preferably 0.01 to 2.0%, more preferably 0.1 to 1.0% of methionine is effective for the high production of DACPC by the microorganisms of the genus Cephalosporium and Emericellopsis. And an addition of at least 0.01%, preferably 0.01 to 1.0%, more preferably 0.1 to 0.5% of cysteine and/or cystine is effective for the high production of DACPC by the microorganisms of the genus Paecilomyces, Arachnomyces, Anixiopsis and Spiroidium.

While the cultivation of the microorganisms can be carried out by any of the stationary and the shake cultural methods, it is generally advantageous to conduct a submerged culture under aerobic conditions. The cultivation temperature is within the range of about 18° to 40°C, preferably within about 22° to 35°C. The pH is maintained at Ph about 2 to 10 and, preferably, within the range of pH 4 to 9. The cultivation is advantageously continued for about 50 to 480 hours, preferably 72 to 336 hours.

Since a major proportion of the elaborated DACPC occurs in the liquid phase of the cultured broth, it is advantageous to remore the mycelium from the broth first by centrifugation or filtration and, then, harvest the desired compound from the supernatant or filtrate. Fractional isolation of DACPC can be achieved by procedures analogous to the procedures routinely used in the fractional recovery of weakly acid organic products or of cephalosporin C and other compounds.

Thus, the fractionation can be achieved with advantage by using, in a suitable combination, chromatography on ion exchange resins, activated carbon, cellulose, silica gel, etc. and gel filtration. For a quantitative determination of DACPC, the procedure for assaying the antibiotic potency of products against an assay organism is employed. Identification of the product is performed by such procedures as elemental analysis, nuclear magnetic resonance spectrometry, infrared spectrometry, ultraviolet spectrometry, paper electrophoresis and thin-layer chromatography.

By using these procedures in combination, DACPC can be isolated as the free compound or its salt.

For further explanation of the present invention, the following examples are given, wherein "part(s)" are based on weight unless otherwise noted and the relationship between part(s) and "part(s) by volume" corresponds to that between "gram(s)" and "milliliter(s)".

EXAMPLE 1

A 2000 parts by volume capacity fermenter is filled with 500 parts by volume of a seed culture medium containing 2% of glucose, 1% of maltose, 1% of glycerol, 2% of cotton seed flour, 1% of corn steep liquor, 0.3% of $(NH_4)_2SO_4$, 0.3% of $NH_4NO_3$, 0.01% of $KH_2PO_4$, 0.05% of $MgSO_4.7H_2O$, 0.005% of $FeSO_4.7H_2O$, 0.01% of NaCl, 0.5% of DL-methionine and 1% of $CaCO_3$. After sterilization, the medium is inoculated with a population of spores from a slant culture of Streptomyces griseus U-25 (ATCC-31031) and incubated at 28°C for 72 hours.

Separately, a 50,000 parts by volume capacity fermentation tank is filled with 30,000 parts by volume of an aqueous medium containing 3% of glucose, 3% of corn starch, 2% of cotton seed flour, 1% of corn steep liquor, 0.3% of $(NH_4)_2SO_4$, 0.3% of $NH_4NO_3$, 0.01% of $KH_2PO_4$, 0.05% of $MgSO_4.7H_2O$, 0.005% of $FeSO_4.7H_2O$, 0.01% of NaCl, 0.5% of DL-methionine and 1% of $CaCO_3$. The tank is sterilized by a routine procedure and allowed to cool. This medium is aseptically inoculated with the above seed culture and incubated at 28°C under sparging and agitation. After 164 hour fermentation, the cultured broth is subjected to filtration, whereupon 25,000 parts by volume of a culture filtrate is obtained. (This filtrate contains 110 μg./ml. of DACPC). The filtrate is adjusted to pH 5 with HCl and adsorbed on a column packed with 8,000 parts by volume of activated carbon. After washing with water, elution is carried out with 20,000 parts by volume of 50% aqueous acetone. The eluate is immediately run onto a column packed with 3,000 parts by volume of ion exchanged resin Amberlite IRA-900 (acetate form) (manufactured by Rohm & Hass Company) and, after washing with water, elution is carried out with 10,000 parts by volume of 0.3 N ammonium acetate. The resultant eluate is applied for a second time to a column of 1,500 parts by volume of activated carbon and, after washing with water, elution is performed with 3,000 parts by volume of 50% aqueous acetone. The resultant eluate is concentrated under reduced pressure to obtain 50 parts by volume of a concentrate.

The above concentrate is applied to a column packed with 3,000 parts by volume of cellulose and eluted with 70% aqueous propanol. The fractions rich in DACPC are pooled and concentrated under reduced pressure.

The concentrate thus obtained is run onto a column packed with 150 parts by volume of activated carbon and, after washing with water, eluted with 300 parts by volume of a 50% aqueous solution of acetone. The eluate is neutralized with sodium hydroxide and concentrated under reduced pressure. To this concentrate is added ethanol, and the mixture is allowed to stand in the cold. The crystals that have separated are harvested by filtration and dehydrated under reduced pressure. The procedure yields 0.670 part of crystals of DACPC sodium salt.

EXAMPLE 2

A 5,000 parts by volume capacity fermenter is filled with 2,500 parts by volume of a culture medium containing 3% of glucose, 3% of corn starch, 0.5% of yeast extract, 1% of cotton seed flour, 0.5% of raw soy bean flour, 0.05% of $MgSO_4.7H_2O$ and 0.5% of $CaCO_3$. After sterilization, the medium is inoculated with *Streptomyces hygroscopicus* U-442(ATCC-31039) and incubated at 28°C under agitation for 144 hours, whereby 820 $\mu$g/ml. of DACPC is accumulated in the cultured broth. Other cephalosporin compounds (e.g. CPC and DCPC) are also produced as by-products. The same treatment as in Example 1 of 2,000 parts by volume of the culture filtrate gives 0.30 part of crystals of sodium salt of DACPC.

EXAMPLE 3

A 2,000 parts by volume capacity fermenter is filled with 500 parts by volume of a seed culture medium containing 5% of glucose, 1.0% of cotton seed flour, 0.5% of raw soybean flour, 0.5% of yeast extract, 0.5% of polypepton and 1% of $CaCO_3$. After sterilization, the medium is inoculated with a population of spores from a slant culture of *Cephalosporium* sp. ATCC-14553 and incubated at 28°C for 96 hours. Separately, 50,000 parts by volume capacity fermentation tank is filled with 30,000 parts by volume of a medium containing 8% of sucrose, 1% of cotton seed flour, 3% of corn steep liquor, 0.5% of DL-methionine, 0.15% of $CaCO_3$ and 0.05% of soybean oil, sterilized in the routine manner and allowed to cool. This medium is aseptically inoculated with the above seed culture and, under sparging and agitation, incubated at 24°C for 168 hours.

After the cultivation has been completed, the broth is withdrawn and filtered to obtain 25,000 parts by volume of a culture filtrate.

This filtrate contains 105 $\mu$g./ml. of DACPC. Furthermore, the filtrate contains penicillin N, CPC and DCPC.

To the filtrate is added penicillinase (manufactured by Schwarz-Mann) to completely decompose penicillin N and, immediately thereafter, the mixture is applied to a column packed with 8,000 parts by volume of Amberlite IRA-900(acetate form) to cause DACPC to be adsorbed thereon. The DACPC thus adsorbed is eluted with 20,000 parts by volume of 0.3 N ammonium acetate and fractions rich in DACPC are collected. This eluate is applied to a column packed with 3,000 parts by volume of activated carbon and, after washing with water, the DACPC adsorbed is eluted with 6,000 parts by volume of a 50% aqueous solution of acetone. The fractions rich in DACPC are pooled, neutralized with NaOH and concentrated to obtain a DACPC-containing concentrate.

This solution contains not only DACPC but also DCPC and CPC. To fractionally remove the latter two, the solution is run onto a column of cellulose and eluted with a 70% aqueous solution of propanol, whereupon CPC, DACPC and DCPC emerge in that order. The DACPC fractions are pooled, concentrated and rechromatographed on a column of cellulose. The DACPC fractions are pooled.

The solution thus obtained is run onto a column of activated carbon and, after washing with water, elution is carried out with a 50% aqueous solution of acetone. The eluate is neutralized with a solution of sodium hydroxide, concentrated and, after the addition of ethanol, allowed to stand in the cold, whereupon DACPC sodium salt precipitates. These crystals are harvested by filtration and dried. The procedure yields 0.520 part of crystals of DACPC.

EXAMPLE 4

A 50,000 parts by volume capacity fermenter is filled with 30,000 parts by volume of a culture medium containing 6% of sucrose, 5% of glucose, 3% of peanuts cake 3% of soy bean flour, 1% of DL-methionine, and 0.15% of $CaCO_3$. After sterilization, the medium is inoculated with *Cephalosporium acremonium* K-186 (ATCC-20416) and incubated at 28°C under aeration and agitation (aeration rate 30,000 parts by volume per minutes; agitation rate 250 r.p.m.) for 190 hours, whereby 1790 $\mu$g/ml. of DACPC is accumulated in the cultured broth. CPC and DCPC are produced as by-products. The same treatment as in Example 3 of this culture broth gives 10.5 parts of crystals of sodium salt of DACPC.

EXAMPLE 5

A 5,000 parts by volume capacity fermenter is filled with 2,500 parts by volume of a culture medium containing 5% of sucrose, 3% of raw soy bean flour, 1% of DL-methionine, 0.15% of $CaCO_3$ and 3% of methyl-oleate. After sterilization, the medium is inoculated with *Cephalosporium polyaleurum* 7-64 (ATCC-20415) and incubated at 24°C under agitation for 192 hours, whereby 560 $\mu$g/ml. of DACPC is accumulated in the cultured broth. CPC and DCPC are also produced as by-products. The same treatment as in Example 3 of 2,000 parts by volume of this culture broth gives 0.250 part of crystals of sodium salt of DACPC.

EXAMPLE 6

A 5,000 parts by volume capacity fermenter is filled with 2,500 parts by volume of a culture medium containing 8% of glucose, 2% of cotton seed flour, 0.5% of DL-methionine and 1% of $CaCO_3$. After sterilization the medium is inoculated with *Emericellopsis microspora* K-163 (ATCC-20422) and incubated at 28°C under agitation for 144 hours, whereby 540 $\mu$g/ml. of DACPC is accumulated in the cultured broth. CPC and DCPC are also produced as by-products. The same treatment as in Example 3 of 2,000 parts by volume of the culture broth gives 0.20 part of crystals of sodium salt of DACPC.

EXAMPLE 7 a. Thirty parts by volume of a seed culture medium containing 5% of glucose, 1% of cotton seed flour, 0.5% of raw soybean flour, 0.5% of yeast extract, 0.5% of peptone and 1% of $CaCO_3$ is distributed into a fermenter with 200 parts by volume capacity. After sterilization, the medium is inoculated with *Paecilomyces carneus* C-2237 (ATCC-20417) and is incubated at 28°C for 72 hours. Then, the seed culture is transferred in 1.5 parts by volume aliquots, into 30 parts by volume of fermentation media. Each of these media is contained in fermenters with 200 parts by volume in capacity which comprises 4% of cotton seed meal, 1% of $CaCO_3$ and one of various carbon sources, the types and amounts of which are indicated below in the Table 5.

b. Thirty (30) parts by volume of a seed culture medium containing 5% of glucose, 1% of cotton seed flour, 0.5% of raw soybean flour, 0.5% of yeast extract, 0.5% of peptone and 1% of $CaCO_3$ is distributed into a fermenter with 200 parts by volume in capacity. After sterilization, the medium is inoculated with *Paecilomyces persicinus* C-3009 (ATCC-20418) and is incubated at 28°C for 72 hours. Then, the seed culture is transferred in 1.5 parts by volume aliquots, into 30 parts by volume of fermentation media. Each of these media is contained in fermenters with 200 parts by volume in capacity which comprises 4% of cotton seed meal, 1% of $CaCO_3$ and one of various carbon sources, the types and amounts of which are indicated below in table 6.

In the case of (a) and (b), when the carbon source is acetic acid, a 40% solution of acetic acid (which has been previously partially neutralized with aqueous ammonia and sterilized) is added at 72 hours, 96 hours, 120 hours of cultivation in an amount of 0.75 part by volume. And when the carbon source is alcohol, ethanol (99.9%) is added at 72 hours, 96 hours, 120 hours of cultivation in an amount of 0.4 part by volume. The cultivation is conducted at 24°C for 168 hours.

After fermentation, each fermentation broth is taken out and centrifuged and the supernatant is assayed for the titers of DACPC and CPC. The results are set forth in Tables 5 and 6.

Table 5

| | | *Paecilomyces carneus* C-2237 | | |
|---|---|---|---|---|
| Carbon source | Initial concent-ration | Amounts of cephalosporin-antibiotics accumulated | | |
| | | DACPC | DCPC | CPC |
| Glucose | 8% | 160 μg/ml. | 35 μg/ml. | 120 μg/ml. |
| Sucrose | 8 | 140 | 20 | 120 |
| Soluble starch | 8 | 100 | 10 | 80 |
| Glycerin | 5 | 85 | 5 | 60 |
| Soybean | 5 | 15 | Not | 10 |
| oil | | | detected | |
| n-Paraffins | 8 | 120 | 25 | 110 |
| Acetic acid | 2 | 25 | Not detected | 5 |

Table 6

| | | *Paecilomyces persicinus* C-3009 | | |
|---|---|---|---|---|
| Carbon source | Initial concent-ration | Amounts of cephalosporin-antibiotics accumulated | | |
| | | DACPC | DCPC | CPC |
| Sucrose | 8% | 90 μg/ml. | 10 μg/ml. | 110 μg/ml. |
| Glucose | 8 | 50 | 15 | 30 |
| Acetic acid | 2 | 10 | Not detected | 15 |
| Ethanol | 2 | 15 | Not detected | 5 |

EXAMPLE 8 a. A 200 parts by volume capacity fermenter is filled with 30 parts by volume of a medium containing 8% of glucose, 2% of cotton seed flour, 1% of $CaCO_3$ and the compound designated by Table 7. After sterilization, each medium is inoculated with *Paecilomyces carneus* C-2237 (IFO-9729) and incubated under agitation at 24°C for 168 hours. After fermentation, the fermentation broth is taken out and centrifuged and the supernatant is assayed for the titers of DACPC.

b. A 200 parts by volume capacity fermenter is filled with 30 parts by volume of a medium containing 8% of glucose, 2% of cotton seed flour, 1% of $CaCO_3$ and the compound designated by Table 7. After sterilization, each medium is inoculated with *Paecilomyces persicinus* C-3009 (ATCC-20418) and incubated under agitation at 24°C for 168 hours. After fermentation, the fermentation broth is taken out and centrifuged and the supernatant is assayed for the titers of DACPC.

c. A 200 parts by volume capacity fermenter is filled with 30 parts by volume of a medium containing 8% of glucose, 2% of cotton seed flour, 1% of $CaCO_3$ and the compound designated by Table 7. After sterilization, each medium is inoculated with *Paecilomyces carneus* C-4053 (IFO-9730) and incubated under agitation at 24°C for 168 hours. After fermentation, the fermentation broth is taken out and centrifuged and the supernatant is assayed for the titers of DACPC.

Table 7

| Compounds added | Concentration in medium | Strains | | |
|---|---|---|---|---|
| | | *Paecilomyces carneus* C-2237 | *Paecilomyces persicinus* C-3009 | *Paecilomyces carneus* C-4053 |
| L-cysteine | 0.3 % | 520 μg/ml. | 310 μg/ml. | 110 μg/ml. |
| L-cystine | 0.3 % | 400 μg/ml. | 220 μg/ml. | 85 μg/ml. |
| None | — | 160 μg/ml. | 90 μg/ml. | 30 μg/ml. |

DCPC and CPC are also produced as by-products.

A 5,000 parts by volume capacity fermenter is filled with 2,500 parts by volume of the same medium as above in (a) containing 0.3% of L-cysteine. After sterilizing the medium is inoculated with *Paecilomyces carneus* C-2237 (ATCC-20417) and cultivated by the same procedure as above in (a). The same treatment as in Example 1 of 2,000 parts by volume of the culture filtrate gives 0.210 part of crystals of sodium salt of DACPC. DCPC and CPC are also produced as by-products.

EXAMPLE 9

A 2,000 parts by volume capacity fermenter is filled with 500 parts by volume of a seed culture medium composed of 5% of sucrose, 1% of cotton seed flour, 3% of corn steep liquor and 0.15% of $CaCO_3$ and, after sterilization, inoculated with *Anixiopsis peruviana* CBS-301.67 from its slant culture and then incubated at 28°C for 96 hours.

Separately, a 50,000 parts by volume capacity fermentation tank is filled with 30,000 parts by volume of a medium composed of 8% of glucose, 2% of cotton seed flour, 05% of DL-methionine and 1% of $CaCO_3$ and the medium is sterilized and allowed to cool in the routine manner. The medium is then aseptically inoculated with the above seed culture and incubated at 28°C and under sparging and agitation (aeration: 30,000 parts by volume/min. under agitation) for 184 hours. Then, the resultant cultured broth is recovered and filtered to removed the mycelium, whereupon 25,000 parts by volume of a culture filtrate is obtained. This filtrate contains 130 µg./ml. of DACPC, 25 µg./ml. of DCPC and 5 µg./ml. of CPC.

The same treatment as in Example 1 of the culture filtrate gives 0.650 part of crystals of sodium salt of DACPC.

EXAMPLE 10

A 5,000 parts by volume capacity fermenter is filled with 2,500 parts by volume of a culture medium containing 8% of glucose, 2% of cotton seed flour, 0.5% DL-methionine 0.3% of L-cysteine and 1% of $CaCO_3$. After sterilization, the medium is inoculated with *Anixiopsis peruviana* CBS-301.67 and incubated at 28°C for 168 hours, whereby 250 µg/ml. of DACPC is accumulated in the cultured broth.

The same treatment as in Example 1 of 2,000 parts by volume of the culture filtrate gives 0.10 part of crystals of sodium salt of DACPC. DCPC and CPC are also produced as by-products.

EXAMPLE 11

A 5,000 parts by volume capacity fermenter is filled with 2,500 parts by volume of a culture medium containing 8% of glucose, 2% of cotton seed flour, 0.5% of DL-methionine 0.3% of L-cystine and 1% of $CaCO_3$. After sterilization, the medium is inoculated with *Anixiopsis peruviana* CBS-301.67 and incubated at 28°C for 168 hours, whereby cultured broth which contains 200 µg/ml. of DACPC is accumulated in the cultured broth. The same treatment as in Example 1 of 2,000 parts by volume of the culture filtrate gives 0.08 part of crystals of sodium salt of DACPC. DCPC and CPC are also produced as by-products.

EXAMPLE 12

A 5,000 parts by volume capacity fermenter is filled with 2,500 parts by volume of a culture medium containing 8% of glucose, 2% of cotton seed flour, 0.5% of DL-methionine and 1% of $CaCO_3$. After sterilization, the medium is inoculated with *Anixiopsis peruviana* K-21 (ATCC-20419) and incubated at 28°C for 168 hours, whereby 1050 µg/ml. of DACPC is accumulated in the cultured broth. The same treatment as in Example 1 of 2,000 parts by volume of the culture filtrate gives 0.420 part of crystals of sodium salt of DACPC. DCPC and CPC are also produced as by-products.

EXAMPLE 13

A 5,000 parts by volume capacity fermenter is filled with 2500 parts by volume of a culture medium containing 8% of sucrose, 1% of cotton seed flour, 3% of corn steep liquor and 1% of $CaCO_3$. After sterilization, the medium is inoculated with *Arachnomyces minimus* K-154 (ATCC-20420) and incubated at 28°C for 168 hours, whereby 1200 µg/ml. of DACPC is accumulated in the cultured broth.

The same treatment as in Example 1 of 2000 parts by volume of the culture filtrate gives 0.500 part of crystals of sodium salt of DACPC. DCPC and CPC are also produced as by-products.

EXAMPLE 14

A 5,000 parts by volume capacity fermenter is filled with 2,500 parts by volume of a medium composed of 8% of sucrose, 1% of cotton seed flour, 3% of corn steep liquor, 0.3% of L-cysteine and 0.15% of $CaCO_3$. After sterilization, the medium is inoculated with *Arachnomyces minimus* CBS-324.70 from its slant culture and incubated at 28°C for 168 hours, whereby 102 µg/ml. of DACPC is accumulated in the cultured broth. The same treatment as in Example 1 of 2,000 parts by volume of the culture filtrate gives 0.045 parts of crystals of sodium salt of DACPC. DCPC and CPC are also produced as by-products.

EXAMPLE 15

A 5,000 parts by volume capacity fermenter is filled with 2,500 parts by volume of a medium composed of 8% of sucrose, 1% of cotton seed flour, 3% of corn steep liquor, 0.3% of L-cystine and 0.15% of $CaCO_3$. After sterilization, the medium is inoculated with *Arachnomyces minimus* CBS-324.70 from its slant culture and incubated at 28°C for 168 hours, whereby 105 µg/ml. of DACPC is accumulated in the cultured broth. The same treatment as in Example 1 of 2,000 parts by volume of the culture filtrate gives 0.048 part of crystals of sodium salt of DACPC. DCPC and CPC are also produced as by-products.

EXAMPLE 16

A 5,000 parts by volume capacity fermenter is filled with 2,500 parts by volume of a medium composed of 8% of sucrose, 1% of cotton seed flour, 3% of corn steep liquor, 0.3% of L-cysteine and 0.15% of $CaCO_3$. After sterilization, the medium is inoculated with *Spiroidium fuscum* IFO-5479 from its slant culture and incubated at 28°C for 184 hours, whereby 145 µg/ml. of DACPC is accumulated in the cultured broth. The same treatment as in Example 1 of 2,000 parts by volume of the culture filtrate gives 0.06 part of crystals of sodium salt of DACPC. DCPC and CPC are also produced as by-products.

EXAMPLE 17

A 5,000 parts by volume capacity fermenter is filled with 2,500 parts by volume of a medium composed of 8% of sucrose, 1% of cotton seed flour, 3% of corn steep liquor, 0.3% of L-cystine and 0.15% of $CaCO_3$. After sterilization, the medium is inoculated with *Spiroidium fuscum* IFO-5479 from its slant culture and incubated at 28°C for 184 hours, whereby 115 μg/ml. of DACPC is accumulated in the cultured broth. The same treatment as in Example 1 of 2,000 parts by volume of the culture filtrate gives 0.05 part of crystals of sodium salt of DACPC. DCPC and CPC are also produced as by-products.

EXAMPLE 18

A 5,000 parts by volume capacity fermenter is filled with 2500 parts by volume of a culture medium containing 8% of sucrose, 1% of cotton seed flour, 3% of corn-steep-liquor and 1% of CaCO$_3$. After sterilization, the medium is inoculated with *Spiroidium fuscum* K-461 (ATCC-20421) and incubated at 28°C for 168 hours, whereby 1020 μg/ml. of DACPC is accumulated in the cultured broth. The same treatment as in Example 1 of 2,000 parts by volume of the culture filtrate gives 0.410 part of crystals of sodium salt of DACPC. DCPC and CPC are also produced as by-products.

What we claim is:

1. A method for producing deacetoxycephalosporin C which comprises cultivating *Streptomyces griseus*, *Streptomyces hygroscopicus*, *Cephalosporium acremonium* K-186 (ATCC-20416) *Emericellopsis microspora* K-163 (ATCC-20422), *Paecilomyces carneus* C-2237 (ATCC-20417), *Paecilomyces carneus* C-4053 (IFO-9730), *Paecilomyces persicinus* C-3009 (ATCC-20418), a microorganism of the genus Anixiopsis, a microorganism of the genus Arachnomyces or a microorganism of the genus Spiroidium, which is capable of producing deacetoxycephalosporin C, in a culture medium containing an assimilable carbon source and a digestible nitrogen source until deacetoxycephalosporin C is accumulated in a substantial amount in the cultured broth, and recovering the accumulated deacetoxycephalosporin C from the broth.

2. A method according to claim 1, wherein the cultivation temperature is 18° to 40°C.

3. A method according to claim 1, wherein the pH of the culture medium is 2 to 10.

4. A method according to claim 1, wherein the medium contains cysteine, cystine or a mixture thereof.

5. A method according to claim 1, wherein the medium contains methionine.

6. A method according to claim 4, wherein the cultivation is carried out with *Paecilomyces carneus* C-2237 (ATCC-20417), *Paecilomyces carneus* C-4053 (IFO-9730), *Paecilomyces persicinus* C-3009 (ATCC-20418), a microorganism of the genus Anixiopsis, a microorgansim of the genus Arachnomyces or a microorganism of the genus Spiroidium.

7. A method according to claim 5, wherein the cultivation is carried out with *Cephalosporium polyaleurum* 7-64 (ATCC-20415), *Cephalosporium acremonium* K-186 (ATCC-20416), or *Emericellopsis microspora* K-163 (ATCC-20422).

8. A method according to claim 1, wherein the microorganism is *Streptomyces griseus*.

9. A method according to claim 1, wherein the microorganism is *Streptomyces hygroscopicus*.

10. A method according to claim 1, wherein the microoganism is *Anixiopsis peruviana*.

11. A method according to claim 1, wherein the microorganism is *Arachnomyces minimus*.

12. A method according to claim 1, wherein the microorganism is *Spiroidium fuscum*.

13. A method according to claim 8, wherein the microorganism is *Streptomyces griseus* U-25 (ATCC-31031).

14. A method according to claim 9, wherein the microorganism is *Streptomyces hygroscopicus* U-442 (ATCC-31039).

15. A method according to claim 1, wherein the microorganism is *Cephalosporium acremonium* K-186 (ATCC-20416).

16. A method according to claim 1, wherein the microorganism is *Cephalosporium polyaleurum* 7-64 (ATCC-20415).

17. A method according to claim 1, wherein the microorganism is *Emericellopsis microspora* K-163 (ATCC-20422).

18. A method according to claim 1, wherein the microorganism is *Paecilomyces carneus* C-2237 (ATCC-20417).

19. A method according to claim 1, wherein the microorganism is *Paecilomyces carneus* C-4053 (IFO-9730).

20. A method according to claim 1, wherein the microorganism is *Paecilomyces persicinus* C-3009 (ATCC-20418).

21. A method according to claim 10, wherein the microorganism is *Anixiopsis peruviana* CBS-301.67.

22. A method according to claim 10, wherein the microorganism is *Anixiopsis peruviana* K-21 (ATCC-20419).

23. A method according to claim 11, wherein the microorganism is *Arachnomyces minimus* CBS-324.70.

24. A method according to claim 11, wherein the microorganism is *Arachnomyces minimus* K-154 (ATCC-20420).

25. A method according to claim 12, wherein the microorganism is *Spiroidium fuscum* IFO-5479.

26. A method according to claim 12, wherein the microorganism is *Spiroidium fuscum* K-461 (ATCC-20421).

27. A method according to claim 1, wherein the microorganism is of the genus Anixiopsis.

28. A method according to claim 1, wherein the microorganism is of the genus Arachnomyces.

29. A method according to claim 1, wherein the microorganism is of the genus Spiroidium.

* * * * *

UNITED STATES PATENT OFFICE
CERTIFICATE OF CORRECTION

Patent No. 3,979,260   Dated August 31, 1976

Inventor(s) Yoshio Nakao; Kazuaki Kitano; Kazuhiko Kintaka; Shigeru Suzuki; Kazuyoshi Katamoto; Kiyoshi Nara It is certified that error appears in the above-identified patent and that said Letters Patent are hereby corrected as shown below:

In claim 1, line 3, after "hygroscopicus," insert --Cephalosporium polyaleurum 7-64 (ATCC-20415),--.

Signed and Sealed this

Fourth Day of July 1978

[SEAL]

Attest:

RUTH C. MASON
Attesting Officer

DONALD W. BANNER
Commissioner of Patents and Trademarks